United States Patent [19]

Kennedy

[11] Patent Number: 5,233,283

[45] Date of Patent: Aug. 3, 1993

[54] LIGHT CURING DEVICE POWER CONTROL SYSTEM

[76] Inventor: John Kennedy, 11 Mollison Court, Guelph, Ontario, Canada, N1C 1A7

[21] Appl. No.: 801,937

[22] Filed: Dec. 3, 1991

[51] Int. Cl.⁵ .................................................. H02J 7/00
[52] U.S. Cl. ......................................... 320/13; 320/2
[58] Field of Search ............... 320/5, 13, 14, 20, 21, 320/22, 23, 24, 35, 36, 37, 38, 48, 2

[56] References Cited

U.S. PATENT DOCUMENTS

| | | | |
|---|---|---|---|
| 3,659,180 | 4/1972 | Urbush | 320/2 |
| 3,792,341 | 2/1974 | Kime, Jr. | 320/13 X |
| 4,563,629 | 1/1986 | Keiper | 320/2 X |
| 4,639,655 | 1/1987 | Westhaver et al. | 320/14 |
| 4,670,701 | 6/1987 | Sako et al. | 320/2 |
| 4,714,868 | 12/1987 | Maruyama et al. | 320/5 |
| 4,727,306 | 2/1988 | Misak et al. | 320/20 X |
| 4,803,416 | 2/1989 | Abiven et al. | 320/14 X |
| 4,806,840 | 2/1989 | Alexander et al. | 320/20 |
| 4,847,513 | 7/1989 | Katz et al. | 320/2 X |
| 4,998,057 | 3/1991 | Shinohara et al. | 320/20 X |
| 5,065,083 | 11/1991 | Owens | 320/13 |

Primary Examiner—Kristine L. Peckman
Attorney, Agent, or Firm—David W. Wong

[57] ABSTRACT

This electrical system is for use in a portable hand-held battery operated light curing device. The system includes a microprocessor which is activated by the battery to provide a series of square wave signals to the light curing lamp such that the light output of the light curing lamp is constant over a selected period of time. The system also provides a fast charging circuit for recharging the battery over a relatively short period of time.

7 Claims, 1 Drawing Sheet

LIGHT CURING DEVICE POWER CONTROL SYSTEM

BACKGROUND OF THE INVENTION

This invention relates to light curing system and particularly relates to a light curing system for portable light curing devices used in dental applications.

Light cured composites have become materials of choice for a large number of dental restorations. These composites are easy to work with, contain no potentially dangerous metals, and are available in a large variety of shades to match the tooth enamel color of the patient. In use, the composite is first applied onto the area on the tooth of the patient and then it can be hardened or photo polymerized by exposing it to a high intensity light of wavelengths between 400 and 500 nanometers. Typically the high intensity light is provided by the light generated by a quartz halogen light source. The light is delivered to the composite at the patient's tooth by an elongated flexible light guide. Such elongated light guide often is awkward to manipulate and restricts the mobility of the dentist. In another curing light construction, the light lamp is incorporated in a hand-held unit which is connected by a power supply cord to a power supply for providing the electrical power for operating the light lamp. The elongated power supply cord in this case again restricts the mobility of the dentist.

Recently, attempts have been made to provide a battery powered portable hand-held light unit. The concept has been to free the dentist or assistant completely for better mobility when performing the light curing operation and to allow easy movement of the light from operatory to operatory. However, such portable curing units have been unsatisfactory, in that the curing light generated by the battery in the unit is not constant. Light cured composites used in dentistry vary in cure depths and speeds from manufacturer to manufacturer, from one shade of color to another and from one fill material to another. Cure times used by dentists as recommended by the composite manufacturers vary from ten seconds to one minute. If multiple restorations are being performed in a patient's mouth there can require up to 8 minutes or longer of light curing time. Undercuring is one of the major causes of restoration failures, and undercuring may lead to post operative sensitivity and/or marginal leakage which may lead to secondary carries. It is therefore an absolute necessity that a battery powered curing light unit should be capable of not only multiple exposures that may result in accumulations of up to 8 minutes or longer ON time, but the battery powered curing light unit must provide a consistent output that the dentist can count on. Only with a consistent light output in the wavelength range of between 400 and 500 nanometers can the dentist judge the curing time exposure required by the shade of the material being used in the restoration and the depth of the material being used in the restoration. In the known portable battery powered light curing device, the electrical power of the battery decreases rapidly with the length and number of ON time, and the intensity of the light output also proportionally decreases accordingly. Thus, the output light intensity is not consistent and is unreliable.

SUMMARY OF THE INVENTION

It is a principal object of the present invention to provide a system which can be incorporated in a portable light curing device to provide a consistent output light intensity.

It is another object of the present invention to provide a system which monitors the activation of curing light by a battery power source.

It is another object of the present invention to provide a portable light curing device which is reliable for multiple dental restoration purposes.

It is yet another object of the present invention to provide a portable light curing device which includes a fast rechargeable system for maintaining the device fully charged in a standby condition.

The electrical system according to the present invention is particularly useful in a portable battery operated light curing device. It comprises a light lamp operative to provide a light energy of a selected level. A battery power source is coupled to the light lamp and is operative to provide the electrical energy for activating the light lamp to generate the light energy. A microprocessor device is coupled to the light lamp and the battery power source and is operative to regulate and monitor the supply of the electrical power to the light lamp in the form of a series of electrical pulse signals.

DETAILED DESCRIPTION OF THE PREFERRED EMBODIMENTS

Figure 1:
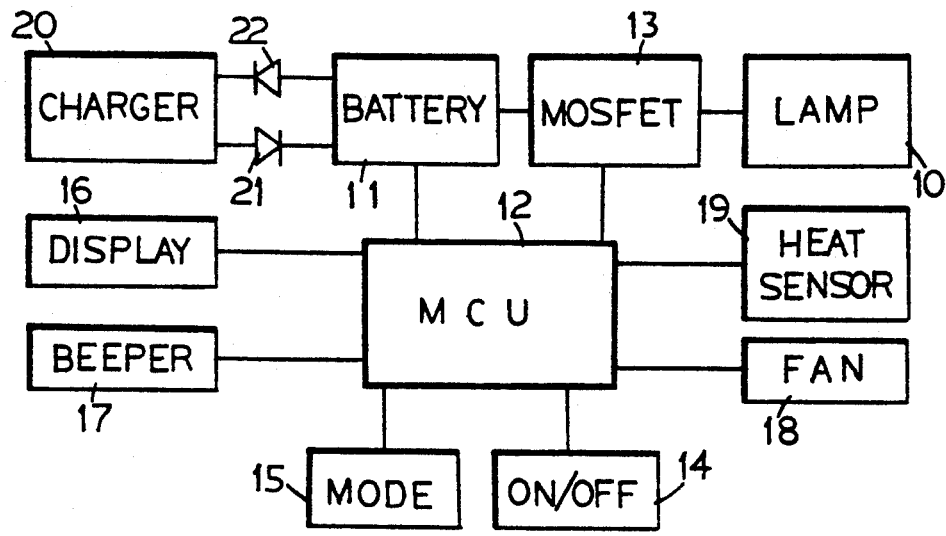
FIG. 1 is a schematic block diagram showing the system of the present invention.
Figure 2:
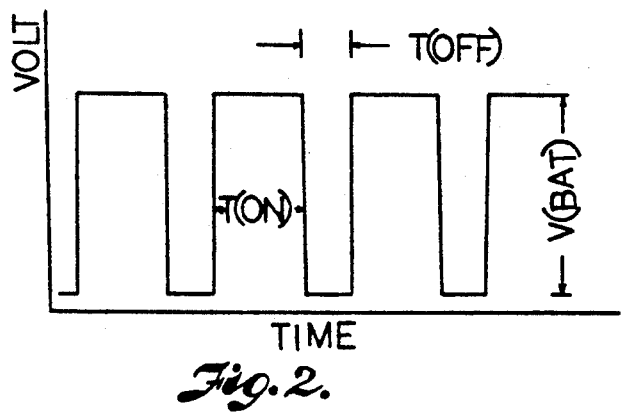
FIG. 2 is a graphical diagram showing the serial of electrical pulse signals supplied to the light lamp by the microprocessor device according to the present invention.

With reference to the drawings, the system according to the present invention which is suitable for incorporating in a portable light curing device is generally shown in FIG. 1. The system comprises a curing light lamp 10 such as a quartz lamp which can be activated by a battery power source 11 to provide a light energy output suitable for light curing purposes. The light energy is typically in the range of from 400 to 500 nanometers. The battery power source 11 may be a nickel cadmium rechargeable battery which can be maintained in a fully charged standby condition by a charging system. The light lamp 10 and the battery 11 are housed in a portable hand-held unit such that it is convenient for a dentist to use it for dental curing purposes. A microprocessor (MCU) device 12 is connected to the battery 11 and the gate terminal of a series pass semiconductor metal oxide semiconductor field effect transistor (MOSFET) 13 which is serially connected between the battery 11 and the light lamp 10. Whenever the system is activated by the operation of an ON/OFF switch 14, the light lamp 10 is energized by a series of controlled pulse voltage to provide a constant light energy output. The voltage applied to the lamp 10 is a series of pulse voltage as shown in FIG. 2 in which the ON time of the pulse voltage is T(on) and the OFF time is T(off). The MCU 12 controls the electrical power supplied to the lamp 10 by controlling the duty cycle i.e. the ratio of T(on) to T(off) of the applied voltage to the lamp 10. The MCU 12 controls this duty cycle according to the battery voltage by generating series of electrical pulse signals to turn the MOSFET 13 on and off. The battery voltage is applied to the lamp 10 when the series pass MOSFET 13 is turned on. The lamp 10 receives no voltage when the MOSFET 13 is turned off.

The OFF time in the applied battery voltage is maintained constant by the MCU 12, while the ON time varies relative to the battery voltage according to the following formula:

$$V(rms)lamp = V(batt) \times \sqrt{T(on)/(T(on)+T(off))}$$

in which V(rms)lamp is the regulated lamp rms voltage which is the equivalent D.C. voltage of the applied pulsed lamp voltage;

V(batt) is the battery voltage;
T(on) is the ON time; and
T(off) is the OFF time.

The microprocessor device 12 includes an analog to digital converter therein which sends output pulses to switch the logic level MOSFET transistor 13 ON and OFF so as to maintain the root mean square (rms) lamp voltage level constant. Once the battery voltage has dropped to a level equal to the rms lamp voltage, the microprocessor device 12 drives the MOSFET transistor 13 to hard ON thereby applying the battery voltage directly to the light lamp 10. In this manner, a constant electrical power is provided to the lamp while the electrical power in the battery may vary with the condition of the battery. The microprocessor device 12 is designed to shut down the curing light lamp 10 if the battery voltage has dropped below a minimum set value. This automatic shut off feature allows the curing light lamp 10 to operate only with the regulated output power and to protect the battery from fully discharged. The microprocessor device 12 will also shut down the system when it detects a fault condition so as to protect the MOSFET transistor 13 and the light lamp 10 from damages.

The length of time the curing light lamp 10 is activated may be selected with a mode selector 15 connected to the microprocessor device 12. Accordingly, the ON time of the light lamp 10 can be set to the required curing time for the particular curing composite used as recommended by its manufacturer. The selected curing time is displayed in a digital display 16 connected to the microprocessor device 12. After a selected curing time is set by the mode selector 15, the display 16 will start to count down as soon as the curing light lamp 10 is activated until it counts to zero and time out. Also, the mode switch 15, when pre-set to zero can actuate the display 16 to show the selected length of curing time, and such selected time would be freezed when it is shut off. A beeper 17 coupled to the microprocessor device 12 will emit a short operating sound signal when the light lamp 10 is turned ON. A double action switch may be used for the ON/OFF switch 14 such that the light lamp 10 can be conveniently turned ON and OFF alternately by pressing the single ON/OFF switch. When the light lamp 10 is turned off, the beeper 17 will emit an extended sound signal to indicate that the system has been shut down. The microprocessor device 12 also controls the voltage supply to a ventilation fan 18 located adjacent to the light lamp 10. Whenever the lamp 10 is activated the ventilation fan 18 will be operated for a predetermined time interval so as to dissipate the heat inherently generated by the lamp 10. A temperature sensor 19 such as a thermistor is located close to the light lamp 10 and it is electrically connected to the microprocessor device 12. The temperature sensor 19 will also cause the system to shut down if the temperature of the lamp 10 exceeds a predetermined allowable limit. The control circuit in the microprocessor device 12 will automatically place the device in its lowest power consumption mode when it is not in use. The microprocessor device 12 also includes a monitor means therein which supervises the input of power from a charger 20 to the battery such that it would not allow the lamp 10 to be activated while the battery is being charged.

The charger 20 is connected to the battery 11 via protection diodes 21 and 22 which allow charges to flow in one direction from the charger to the battery and they prevent the charges from the battery to flow in the reverse direction back to the charger the charger connection terminals.

The charger 20 may be provided in a base on which the portable light unit is normally placed, when it is not in use. Associated terminals are provided in the light curing unit and the charger base such that they will engage one another when the light curing unit is placed onto the base unit so as to ensure that the battery 10 is recharged to its full power.

The unique charger 20 of the present invention can charge the battery 11 in a short period of time. Such short charge time enhances the charge efficiency and the battery capacity. Since nickel cadmium batteries cannot sustain indefinite overcharge at fast charge rates, the fast charger 20 is required to terminate the higher rate of charging before the battery receives too much overcharge. This charger 20 does not rely on arbitrary factors such as time to determine the optimum point to discontinue the high rate of charge. It continually monitors the battery voltage and detects the appropriate time to discontinue the high current flow to the battery by employing the voltage decrement cut off. The charger 20 detects a specific drop in the battery voltage from the highest potential it has reached and switches to a lower trickle charging rate.

Figure 3:
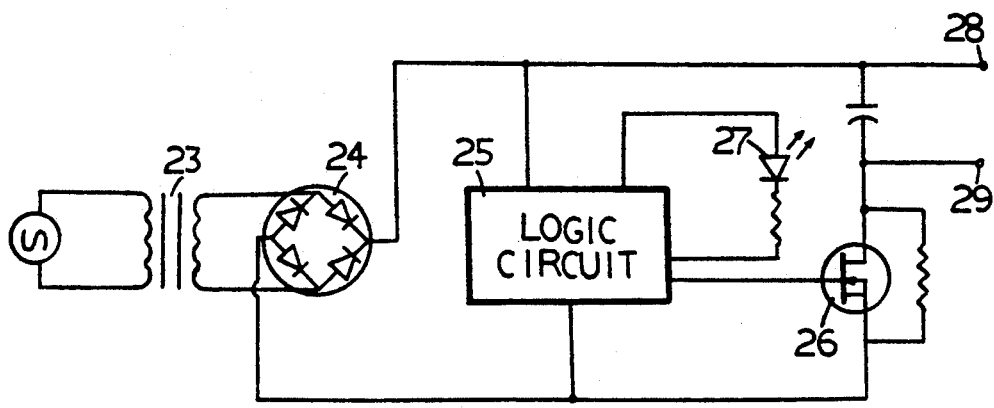
FIG. 3 is an electrical partial schematic and block diagram showing the charging system for the battery according to the present invention.

The construction of the charger 20 is shown in the schematic diagram in FIG. 3. The charger 20 comprises a stepdown transformer 23 for reducing the common alternating current voltage to a lower secondary voltage. The low secondary voltage is then converted to a direct current voltage by a full wave rectifier bridge circuit 24. The charging of the battery 11 is controlled by a logic circuit 25 which is connected to the gate of a MOSFET transistor 26. The battery 11 is connected between the drain pin of the MOSFET transistor 26 and the positive side of the charging voltage from the rectifier bridge circuit 24. The control logic circuit 25 monitors and regulates the charging current by providing a gate drive voltage to the MOSFET transistor 26. The regulated current is set to a selected level typically about 550 milliamperes to charge the battery 10 in a relatively short time period of typically one hour. Once the logic circuit 25 has detected the battery 10 as fully charged, the current is switched to a low trickle rate and a light emitting diode 27 is actuated to indicate that the battery 10 is fully charged. This trickle charge rate will not over-heat or stress the battery and it maintains the battery 10 in a fully charged state.

The logic circuit 25 also provides a short delay before current commences to flow from the charger 20 to the battery 11 after the connection of the battery is made, such delay eliminates arcing and contact wear with the formation of a rough contact surface commonly referred to as "pitting" at the battery connection terminals 28 and 29. The logic circuit 25 will cause the LED diode 27 to blink once to indicate the charger is in the ready state after a small time delay when the battery 11 is removed from the charger 20.

While I have illustrated in the drawings a specific system constituting the preferred embodiment of the invention, it will be appreciated that various modifications may be made in the sequence of steps of the method and in the form of the system, and that equivalent methods, elements and mechanisms may be substituted therefor without departing from the scope of the invention. All such changes, including reversals of parts and the use of certain features, all fall within the spirit and scope of the invention as defined in the appended claims.

Having thus described my invention, I claim:

1. An electrical system located in a portable battery operated light generating device comprising,
   a light lamp means operative to generate a light energy output,
   a battery means coupled to said light lamp means and operative to provide electrical voltage for activating said light lamp means,
   microprocessor means coupled to said light lamp means and to said battery means, and in response to the energy condition in said battery means to generate a series of electrical pulse signals,
   transistor means connected to said microprocessor means and to said battery means, said transistor means receiving said pulse signals from said microprocessor means to operate in a series of varying ON and constant OFF intervals to conduct said pulse signals to said light lamp means for maintaining the light output from said light lamp means at a constant level, and
   mode selector means coupled to said microprocessor means and operative to control the length of time said light lamp means being activated by said electrical voltage.

2. An electrical system according to claim 1 including a display means connected to said microprocessor means, said display means operating to display said length of time selected, and said display means operating to count down said length of time when said light lamp means is activated, and said microprocessor means operating to shut off said light lamp means when said display means has counted down to zero.

3. An electrical system according to claim 2 including a sound signal means coupled to said microprocessor means, said sound signal means being responsive to the activation of said light lamp means to emit a sound signal in a predetermined interval during the operation of said light lamp means for indicating said system is operating in a normal condition.

4. An electrical system according to claim 3 including a heat sensor means located in said light curing device, said heat sensor means being connected to said microprocessor means and being operative to disable said system when an abnormal temperature condition is detected from said light lamp means.

5. An electrical system according to claim 4 including a ventilation fan means coupled to said microprocessor means and being operative by said microprocessor means to cool said light lamp means.

6. An electrical system according to claim 5 including a charger means located in a base unit whereupon said light curing device is normally disposed, said charger means comprising a transformer means for reducing high voltage alternate current to a secondary low voltage, a rectifier means coupled to said transformer means for converting said secondary low voltage to a direct current voltage, a logic circuit means coupled to said rectifier means and being operative to activate a monitoring transistor means connected between said rectifier means and connection terminals of said battery means whereby said monitoring transistor means operates to conduct said direct current voltage to said connection terminals for charging said battery means in a substantially high charging rate.

7. An electrical system according to claim 6 including a light indicator means coupled to said logic circuit means, said light indicator means being operative to emit a light signal to indicate said battery means being charged.

* * * * *